United States Patent [19]
Taylor et al.

[11] Patent Number: 6,136,771
[45] Date of Patent: Oct. 24, 2000

[54] COMPOSITIONS CONTAINING A HIGH PERCENT SATURATION CONCENTRATION OF ANTIBACTERIAL AGENT

[75] Inventors: Timothy J. Taylor, Phoenix; Earl P. Seitz, Jr., Scottsdale; Priscilla S. Fox, Phoenix, all of Ariz.

[73] Assignee: The Dial Corporation, Scottsdale, Ariz.

[21] Appl. No.: 09/425,521

[22] Filed: Oct. 22, 1999

Related U.S. Application Data

[63] Continuation-in-part of application No. 09/338,654, Jun. 23, 1999.

[51] Int. Cl.[7] ............................. C11D 3/48; C11D 3/43
[52] U.S. Cl. ..................... 510/388; 510/130; 510/131; 510/138; 510/151; 510/342; 510/382; 510/398; 510/432
[58] Field of Search ..................... 510/130, 131, 510/138, 151, 342, 382, 388, 398, 432

[56] References Cited

U.S. PATENT DOCUMENTS

| | | | |
|---|---|---|---|
| 4,093,745 | 6/1978 | Wood et al. | 424/358 |
| 4,111,844 | 9/1978 | Polony et al. | 252/106 |
| 4,350,605 | 9/1982 | Hughett | 252/305 |
| 4,518,517 | 5/1985 | Eigen et al. | 252/107 |
| 4,666,615 | 5/1987 | Disch et al. | 252/11 |
| 4,675,178 | 6/1987 | Klein et al. | 424/65 |
| 4,702,916 | 10/1987 | Geria | 424/400 |
| 4,822,602 | 4/1989 | Sabatelli | 424/65 |
| 4,832,861 | 5/1989 | Resch | 252/106 |
| 4,851,214 | 7/1989 | Walters et al. | 424/65 |
| 4,954,281 | 9/1990 | Resch | 252/107 |
| 4,975,218 | 12/1990 | Rosser | 252/117 |
| 5,006,529 | 4/1991 | Resch | 514/721 |
| 5,057,311 | 10/1991 | Kamegai et al. | 424/70 |
| 5,147,574 | 9/1992 | MacGilp et al. | 252/108 |
| 5,158,699 | 10/1992 | MacGilp et al. | 252/132 |
| 5,234,618 | 8/1993 | Kamegai et al. | 252/106 |
| 5,415,810 | 5/1995 | Lee et al. | 252/545 |
| 5,417,875 | 5/1995 | Nozaki | 252/106 |
| 5,441,671 | 8/1995 | Cheney et al. | 252/549 |
| 5,462,736 | 10/1995 | Rech et al. | 424/401 |
| 5,480,586 | 1/1996 | Jakubicki et al. | 252/545 |
| 5,635,462 | 6/1997 | Fendler et al. | 510/131 |
| 5,635,468 | 6/1997 | Fowler | 510/406 |
| 5,646,100 | 7/1997 | Haugk et al. | 510/131 |
| 5,653,970 | 8/1997 | Vermeer | 424/70.24 |
| 5,681,802 | 10/1997 | Fujiwara et al. | 510/130 |
| 5,716,626 | 2/1998 | Sakurai et al. | 424/401 |
| 5,728,756 | 3/1998 | Gaffar et al. | 524/139 |
| 5,730,963 | 3/1998 | Hilliard, Jr. et al. | 424/65 |
| 5,824,650 | 10/1998 | De Lacharriere et al. | 514/15 |
| 5,837,272 | 11/1998 | Fierro, Jr. et al. | 424/401 |
| 5,851,974 | 12/1998 | Sandhu | 510/235 |
| 5,863,524 | 1/1999 | Mason et al. | 424/65 |
| 5,871,718 | 2/1999 | Lucas et al. | 424/65 |
| 5,888,524 | 3/1999 | Cole | 424/402 |
| 5,919,438 | 7/1999 | Saint-Leger | 424/70.1 |
| 5,955,408 | 9/1999 | Kaiser et al. | 510/131 |
| 5,985,294 | 11/1999 | Peffly | 424/401 |

FOREIGN PATENT DOCUMENTS

| | | | |
|---|---|---|---|
| 0 505 935 | 9/1992 | European Pat. Off. | C11D 3/48 |
| WO 95/09605 | 4/1995 | WIPO | A61K 7/50 |
| WO 95/32705 | 12/1995 | WIPO | A61K 7/50 |
| WO 96/06152 | 2/1996 | WIPO | C11D 3/00 |
| WO 97/46218 | 12/1997 | WIPO | A61K 7/48 |
| WO 98/0110 | 1/1998 | WIPO | A61K 7/48 |
| WO 98/55096 | 12/1998 | WIPO | A61K 7/50 |
| WO 98/55097 | 12/1998 | WIPO | A61K 7/50 |

OTHER PUBLICATIONS

Allawala et al., *Journal of the American Pharmaceutical Association*, vol. XLII, No. 5, pp. 267–275 (1953).

Mitchell, *J. Pharm. Pharmacol*, 16, pp. 533–537 (1964).

*Primary Examiner*—Yogendra Gupta
*Assistant Examiner*—Charles Boyer
*Attorney, Agent, or Firm*—Marshall, O'Toole, Gerstein, Murray & Borun

[57] ABSTRACT

Antibacterial compositions having excellent antibacterial effectiveness and a reduced amount of disinfecting alcohol are disclosed. The antibacterial compositions contain a phenolic antibacterial agent, a disinfecting alcohol, a gelling agent, and water, wherein a percent saturation of the antibacterial agent in a continuous aqueous phase of the composition is at least 25%.

57 Claims, No Drawings

COMPOSITIONS CONTAINING A HIGH PERCENT SATURATION CONCENTRATION OF ANTIBACTERIAL AGENT

CROSS REFERENCE TO RELATED APPLICATIONS

This is a continuation-in-part of U.S. patent application Ser. No. 09/338,654, filed Jun. 23, 1999, pending.

FIELD OF THE INVENTION

The present invention is directed to antibacterial compositions, like personal care compositions, and particularly hand sanitizer gels, having improved antibacterial effectiveness. More particularly, the present invention is directed to hand sanitizer gels comprising an antibacterial agent and a relatively low amount of a disinfecting alcohol, and that provide a substantial reduction, e.g., greater than 99%, in Gram positive and Gram negative bacterial populations within one minute.

BACKGROUND OF THE INVENTION

Antibacterial personal care compositions are known in the art. Especially useful are antibacterial cleansing compositions, which typically are used to cleanse the skin and to destroy bacteria and other microorganisms present on the skin, especially the hands, arms, and face of the user.

Another class of antibacterial personal care compositions is the hand sanitizer gels. This class of compositions is used primarily by medical personnel to disinfect the hands and fingers. The hand sanitizer gel is applied to, and rubbed into, the hands and fingers, and the composition is allowed to evaporate from the skin. Wiping of the composition from the skin is not necessary because the high alcohol content of present-day hand sanitizer gels leads to a fast and essentially complete evaporation of the composition from the skin.

Antibacterial compositions in general are used, for example, in the health care industry, food service industry, meat processing industry, and in the private sector by individual consumers. The widespread use of antibacterial compositions indicates the importance consumers place on controlling bacteria and other microorganism populations on skin. It is important, however, that antibacterial compositions provide a substantial and broad spectrum reduction in microorganism populations quickly and without problems associated with toxicity and skin irritation.

In particular, antibacterial cleansing compositions typically contain an active anti-bacterial agent, a surfactant, and various other ingredients, for example, dyes, fragrances, pH adjusters, thickeners, skin conditioners, and the like, in an aqueous and/or alcoholic carrier. Several different classes of antibacterial agents have been used in antibacterial cleansing compositions. Examples of antibacterial agents include a bisguanidine (e.g., chlorhexidine digluconate), di-phenyl compounds, benzyl alcohols, trihalocarbanilides, quaternary ammonium compounds, ethoxylated phenols, and phenolic compounds, such as halo-substituted phenolic compounds, like PCMX (i.e., p- chloro-m-xylenol) and triclosan (i.e., 2,4,4'-tri-chloro-2'hydroxydiphenylether). Present-day antimicrobial compositions based on such antibacterial agents exhibit a wide range of antibacterial activity, ranging from low to high, depending on the microorganism to be controlled and the particular antibacterial composition.

Hand sanitizer gels contain a high percentage of an alcohol, like ethanol. At the high percent of alcohol present in the gel, the alcohol itself acts as a disinfectant. In addition, the alcohol quickly evaporates to obviate wiping or rinsing skin treated with the sanitizer gel. Hand sanitizer gels containing a high percentage of an alcohol, i.e., about 40% or greater by weight of the composition, however, have a tendency to dry and irritate the skin.

Most commercial antibacterial compositions generally offer a low to moderate antibacterial activity. Antibacterial activity is assessed against a broad spectrum of microorganisms, including both Gram positive and Gram negative microorganisms. The log reduction, or alternatively the percent reduction, in bacterial populations provided by the antibacterial composition correlates to antibacterial activity. A log reduction of 3–5 is most preferred, a 1–3 log reduction is preferred, whereas a log reduction of less than 1 is least preferred, for a particular contact time, generally ranging from 15 seconds to 5 minutes. Thus, a highly preferred antibacterial composition exhibits a 3–5 log reduction against a broad spectrum of microorganisms in a short contact time.

It should be noted that high log reductions have been achieved at pH values of 4 and 9, but such log reductions are attributed at least in part to these relatively extreme pH values. Compositions having such extreme pH values can irritate the skin and other surfaces, and, therefore, typically are avoided, especially as hand sanitizer compositions which typically are not wiped or rinsed from the skin after use. It has been difficult to impossible to achieve a high log reduction using an antibacterial composition having a neutral pH of about 5 to about 8, and especially about 6 to about 8, without simultaneously incorporating a high percentage of an alcohol.

For example, WO 98/01110 discloses compositions comprising triclosan, surfactants, solvents, chelating agents, thickeners, buffering agents, and water. WO 98/01110 is directed to reducing skin irritation by employing a reduced amount of surfactant.

Fendler et al. U.S. Pat. No. 5,635,462 discloses compositions comprising PCMX and selected surfactants. The compositions disclosed therein are de- void of anionic surfactants and nonionic surfactants.

WO 97/46218 and WO 96/06152 disclose compositions based on triclosan, organic acids or salts, hydrotropes, and hydric solvents.

EP 0 505 935 discloses compositions con- taining PCMX in combination with nonionic and anionic surfactants, particularly nonionic block copolymer surfactants.

WO 95/32705 discloses a mild surfactant combination that can be combined with antibacterial compounds, like triclosan.

WO 95/09605 discloses antibacterial compositions containing anionic surfactants and alkylpolyglycoside surfactants.

WO 98/55096 discloses antimicrobial wipes having a porous sheet impregnated with an antibacterial composition containing an active anti-microbial agent, an anionic surfactant, an acid, and water, wherein the composition has a pH of about 3.0 to about 6.0.

N. A. Allawala et al., *J. Amer. Pharm. Assoc.—Sci. Ed.*, Vol. XLII, no. 5, pp. 267–275, (1953) discloses the antibacterial activity of active antibacterial agents in combination with surfactants.

A. G. Mitchell, *J. Pharm. Pharmacol.*, Vol. 16, pp. 533–537, (1964) discloses compositions containing PCMX and a nonionic surfactant that exhibit antibacterial activity. The compositions disclosed in the Mitchell publication exhibit antibacterial activity in at least 47 minutes contact time, thus the compositions are not highly effective.

With respect to hand sanitizer gels, Osborne et al. U.S. Pat. No. 5,776,430 discloses a topical antimicrobial cleaner containing chlorhexidine and an alcohol. The compositions contain about 50% to 60%, by weight, denatured alcohol and about 0.65 to 0.85%, by weight, chlorhexidine. The composition is applied to the skin, scrubbed into the skin, then rinsed from the skin.

European Patent Application 0 604 848 discloses a gel-type hand disinfectant containing an antimicrobial agent, 40% to 90% by weight of an alcohol, and a polymer and a thickening agent in a combined weight of not more than 3% by weight. The gel is rubbed into the hands and allowed to evaporate to provide disinfected hands. As illustrated in EP 0 604 848, the amount and identity of the antibacterial agent is not considered important because the hand sanitizer gels contain a high percentage of an alcohol to provide antibacterial activity. The disclosed compositions often do not provide immediate sanitization and do not provide residual antibacterial efficacy.

In general, hand sanitizer gels typically contain: (a) at least 60% by weight ethanol or a combination of lower alcohols, such as ethanol and isopropanol, (b) water, (c) a gelling polymer, such as a crosslinked polyacrylate material, and (d) other ingredients, such as skin conditioners, fragrances, and the like. Hand sanitizer gels are used by consumers to effectively sanitize the hands, without, or after, washing with soap and water, by rubbing the hand sanitizer gel on the surface of the hands. Current commercial hand sanitizer gels rely on high levels of alcohol for disinfection and evaporation, and thus suffer from disadvantages. Specifically, current hand sanitizer gels have a tendency to dry and irritate the skin because of the high levels of alcohol employed in the compositions.

Also, because of the volatility of ethyl alcohol, the primary active disinfectant does not remain on the skin after use, thus failing to provide a persistent, or residual, antibacterial effect.

At alcohol concentrations below 60%, ethyl alcohol is not recognized as an antiseptic. Thus, in compositions containing less than 60% alcohol, an additional antibacterial compound must be present to provide antibacterial activity. Prior disclosures, however, have not addressed the issue of which composition ingredient in such an antibacterial composition provides bacterial control. Therefore, for formulations containing a reduced alcohol concentration, the selection of an antibacterial agent that provides both a rapid antibacterial effect and a persistent antibacterial benefit is difficult. Prior compositions also have not provided an effective, fast, and broad spectrum control of bacteria at a neutral pH of about 5 to about 8, and especially at about 6 to about 8.

An efficacious antibacterial composition has been difficult to achieve because of the properties of the antibacterial agents. For example, several active antibacterial agents, like phenols, have an exceedingly low solubility in water, e.g., triclosan solubility in water is about 5 to 10 ppm (parts per million). The solubility of the antibacterial agent is increased by adding alcohols to the composition. However, an increase in solubility of the antimicrobial agent, and in turn, the amount of antibacterial agent in the composition, does not necessarily lead to an increased antibacterial efficacy.

Accordingly, a need exists for an antibacterial composition, particularly a hand sanitizer composition, that is highly efficacious against a broad spectrum of Gram positive and Gram negative bacteria in a short time period, and that provides residual antibacterial activity, wherein the antibacterial activity is attributed primarily, or solely, to the presence of the active antibacterial agent in the composition. The present invention is directed to such antibacterial compositions.

SUMMARY OF THE INVENTION

The present invention relates to antibacterial compositions that provide a substantial reduction in Gram positive and Gram negative bacteria in less than about one minute. More particularly, the present invention relates to antimicrobial compositions containing an active antibacterial agent, a disinfecting alcohol, a gelling agent, and water, wherein the antibacterial agent is present in an amount of at least 50% of saturation, when measured at room temperature. The present invention also relates to antimicrobial compositions contain- ing an active antibacterial agent, a disinfecting alcohol, a gelling agent, a hydrotrope, and water, wherein the antibacterial agent is present in an amount of at least 25% of saturation, when measured at room temperature.

Accordingly, one aspect of the present invention is to provide a liquid, antibacterial composition comprising: (a) about 0.05% to about 5%, by weight, of an antibacterial agent; (b) about 1% to about 40%, by weight, of a disinfecting alcohol, like a $C_{1-6}$ alcohol; (c) about 0.01% to about 5% by weight of a gelling agent, like a colloidal or a polymeric gelling agent; and (d) water, wherein the antibacterial agent is present in the composition in an amount of at least 50% of saturation concentration, when measured at room temperature.

Another aspect of the present invention is to provide an alternative embodiment of the antibacterial composition, wherein the composition comprises:

(a) about 0.05% to about 5%, by weight, of an antimicrobial agent;

(b) about 1% to about 40%, by weight, of a disinfecting alcohol;

(c) about 0.01% to about 5%, by weight, of a gelling agent;

(d) 0.1% to about 30%, by weight, of a hydrotrope; and (e) water, wherein the antimicrobial agent is present in the composition in an amount of at least 25% of saturation concentration, when measured at room temperature.

Still another aspect of the present invention is to provide another alternative embodiment of the antibacterial composition, wherein the composition comprises:

(a) 0.05% to about 5%, by weight, of an antimicrobial agent;

(b) about 1% to about 40%, by weight, of a disinfecting alcohol; and (c) water, wherein the composition contains the disinfecting alcohol and an optional polyhydric solvent in an amount sufficient to solubilize the antimicrobial agent, and wherein the antimicrobial agent is present in the composition in an amount of at least 25% of the saturation concentration, when measured at room temperature.

Yet another aspect of the present invention is to provide an antibacterial composition, like a hand sanitizer composition, that exhibits a log reduction against Gram positive bacteria (i.e., S. aureus) of at least 2 after 30 seconds of con- tact.

Still another aspect of the present invention is to provide an antibacterial composition that exhibits a log reduction against Gram negative bacteria (i.e., *E. coli*) of at least 2.5 after 30 seconds of contact.

Another aspect of the present invention is to provide an antibacterial composition that exhibits a substantial log reduction against Gram positive and Gram negative bacteria, and has a pH of about 5 to about 8.

Another aspect of the present invention is to provide consumer products based on an antibacterial composition of the present invention, for example, a body splash, a surgical scrub, a wound care agent, a hand sanitizer gel, a disinfectant, a hard surface sanitizer, and the like.

A further aspect of the present invention is to provide a method of reducing the Gram positive and/or Gram negative bacteria populations on animal tissue, including human tissue, by contacting the tissue, like the dermis, with a composition of the present invention for a sufficient time, such as about 15 seconds to 5 minutes, to reduce the bacteria level to a desired level, and to provide a residual control of bacteria levels. The composition can be wiped or rinsed from the skin. Preferably, the composition is allowed to remain on the skin until the volatile components of the composition evaporate.

The above and other novel aspects and advantages of the present invention are illustrated in the following, nonlimiting detailed description of the preferred embodiments.

DETAILED DESCRIPTION OF THE PREFERRED EMBODIMENTS

Personal care products incorporating an active antibacterial agent have been known for many years. Since the introduction of antibacterial personal care products, many claims have been made that such products provide antibacterial properties. However, to be most effective, an antibacterial composition should provide a high log reduction against a broad spectrum of organisms in as short a contact time as possible. It would also be beneficial if the antibacterial composition provided a residual bacterial control.

As presently formulated, commercial liquid antibacterial soap compositions provide a poor to marginal time kill efficacy, i.e., rate of killing bacteria. Table 1 summarizes the kill efficacy of commercial products, each of which contains about 0.2% to 0.3%, by weight, triclosan (an antibacterial agent), and a surfactant.

TABLE 1

Time Kill Efficacy of Commercial Liquid Hand Soaps

| | Organism (Log Reductions after 1 Minute Contact Time) | | |
|---|---|---|---|
| | Gram Positive *S. aureus* | Gram negative *E. coli* | Gram negative *K. pneum.* |
| Commercial Product A | 1.39 | 0.00 | 0.04 |
| Commercial Product B | 2.20 | 0.00 | 0.01 |
| Commercial Product C | 1.85 | 0.00 | 0.00 |

Antibacterial hand sanitizer compositions typically do not contain a surfactant and rely upon a high concentration of an alcohol to control bacteria. The alcohols evaporate and, therefore, cannot provide residual bacterial control. The alcohols also can dry and irritate the skin.

Present-day products especially lack efficacy against Gram negative bacteria, such as *E. coli*, which are of particular concern to human health. The present invention, therefore, is directed to antibacterial compositions having an exceptionally high broad spectrum antibacterial efficacy, as measured by a rapid kill of bacteria (i.e., time kill), and which provide a persistent kill.

The present antibacterial compositions provide excellent time kill efficacy and a persistent kill compared to prior sanitizer compositions that incorporate a high percentage of an alcohol, i.e., 40% or greater, by weight. The basis of this improved time kill is the discovery that the antimicrobial efficacy of an active agent can be correlated to the rate at which the agent has access to an active site on the microbe. The driving force that determines the rate of agent transport to the site of action is the difference in chemical potential between the site at which the agent acts and the aqueous phase. Alternatively stated, the microbicidal activity of an active agent is proportional to its thermodynamic activity in the aqueous phase. Accordingly, thermodynamic activity, as opposed to concentration, is the more important variable with respect to antimicrobial efficacy. As discussed more fully hereafter, thermodynamic activity is conveniently correlated to the percent saturation of the active antibacterial agent in the continuous aqueous phase of the composition.

Many compounds have a solubility limit in aqueous solutions termed the "saturation concentration," which varies with temperature. Above the saturation concentration, the compound precipitates from solution. Percent saturation is the measured concentration in solution divided by the saturation concentration. The concentration of a compound in aqueous solution can be increased over the saturation concentration in water by the addition of compounds like surfactants, solvents, and hydrotropes. Surfactants not only increase the solubility of antibacterial compounds in the continuous aqueous phase of the composition, but also form micelles, and can solubilize antibacterial compounds in the micelles.

The % saturation of an active antibacterial agent in any composition, including a surfactant-containing composition, ideally can be expressed as:

$$\% \text{ saturation} = [C/C_S] \times 100\%$$

wherein C is the concentration of antibacterial agent in the composition and $C_S$ is the saturation concentration of the antibacterial agent in the composition at room temperature. The percent saturation, or alternatively the relative thermodynamic activity or relative chemical potential, of an antibacterial active agent dissolved in a composition is the same everywhere within the composition. Thus, the terms percent saturation of the antibacterial agent "in a composition," "in the aqueous continuous phase of a composition," and "in the micellar pseudophase of a composition" are interchangeable, and are used as such throughout this disclosure.

Maximum antibacterial efficacy is achieved when the difference in thermodynamic activities of the active antibacterial agent between the composition and the target organism is maximized (i.e., when the composition is more "saturated" with the active ingredient). A second factor affecting antibacterial activity is the total amount of available antibacterial agent present in the composition, which can be thought of as the "critical dose." It has been found that the total amount of active agent in the continuous aqueous phase of a composition greatly influences the time in which a desired level of antibacterial efficacy is achieved, given equal thermodynamic activities. Thus, the two key factors affecting the antibacterial efficacy of an active agent in a composition are: (1) its availability, as dictated by its thermodynamic activity, i.e., percent saturation in the continuous aqueous phase of a composition, and (2) the total amount of avail- able active agent in the solution.

To summarize, the thermodynamic activity, or percent saturation, of an antibacterial agent in the continuous aqueous phase of a composition drives antibacterial activity. Further, the total amount of available active agent determines the ultimate extent of efficacy. In compositions wherein the active agent is present in micelles, the active agent is not directly available for antibacterial activity. For such compositions, the percent saturation of the active agent in the composition, or alternatively the percent saturation of the active agent in the continuous aqueous phase of the composition, determines antibacterial efficacy.

The present compositions are antibacterial compositions having an improved effectiveness against both Gram negative and Gram positive bacteria, that exhibit both a rapid and a persistent bacteria kill. As illustrated in the following embodiments, an antibacterial composition of the present invention comprises: (a) about 0.05% to about 5%, by weight, of an antibacterial agent; (b) about 1% to about 40%, by weight, of a disinfecting alcohol; (c) about 0.01% to about 5%, by weight, of a gelling agent; (d) an optional hydrotrope; and (e) water. The present compositions also can contain an optional polyhydric solvent. The compositions have a percent saturation of antibacterial agent in the continuous phase of at least about 25%, when measured at room temperature. The compositions exhibit a log reduction against Gram positive bacteria of about 2 after 30 seconds contact. The compositions exhibit a log reduction against Gram negative bacteria of about 2.5 after 30 seconds contact. The compositions also are mild, and provide a persistent kill because it is not necessary to rinse or wipe the compositions from the skin.

In accordance with the present invention, the antibacterial compositions comprise an active antibacterial agent, a disinfecting alcohol, a gelling agent, and water as the carrier. The compositions can further include a hydrotrope and additional optional ingredients disclosed hereafter, like polyhydric solvents, pH adjusters, dyes, skin conditioners, vitamins, and perfumes. The present compositions are free of surfactants, i.e., contain 0% to about 0.5%, by weight, of compounds that exhibit surface activity.

Antibacterial Agent

An antibacterial agent is present in a composition of the present invention in an amount of about 0.05% to about 5%, and preferably about 0.1% to about 4%, by weight of the composition. To achieve the full advantage of the present invention, the antibacterial agent is present in an amount of about 0.25% to about 2%, by weight, of the composition.

The antibacterial compositions can be ready to use compositions, which typically contain 0.05% to about 2%, preferably 0.1% to about 1.5%, and most preferably about 0.1% to about 1%, of an antibacterial agent, by weight of the composition. The antibacterial compositions also can be formulated as concentrates that are diluted before use with one to about 50 parts water to provide an end use composition. The concentrated compositions typically contain greater than about 0.05% and up to about 5%, by weight, of the antibacterial agent. Applications also are envisioned wherein the end use composition contains greater than 2%, by weight, of the antibacterial agent.

As discussed above, the absolute amount of antibacterial agent present in the composition is not as important as the amount of available antibacterial agent in the composition. The amount of available antibacterial agent in the composition is related to the identity of the disinfecting alcohol in the composition, the amount of antibacterial agent in the composition, and the presence and amount of gelling agent and optional ingredients in the composition.

To achieve the desired bacteria kill in a short contact time, like 15 to 60 seconds, the composition contains an amount of antibacterial agent that is at least about 25%, and preferably at least about 50%, and more preferably at least about 75%, of the saturation concentration of the antibacterial agent in the composition, when measured at room temperature. To achieve the full advantage of the present invention, the composition is about 95% to 100% saturated with the antibacterial agent. The method of determining percent saturation of antibacterial agent in the composition is disclosed hereafter.

The antimicrobial agents useful in the present invention are phenolic compounds exemplified by the following classes of compounds:

(a) 2-Hydroxydiphenyl compounds

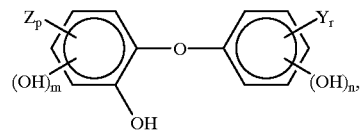

wherein Y is chlorine or bromine, Z is $SO_2H$, $NO_2$, or $C_1$–$C_4$ alkyl, r is 0 to 3, o is 0 to 3, p is 0 or 1, m is 0 or 1, and n is 0 or 1.

In preferred embodiments, Y is chlorine or bromine, m is 0, n is 0 or 1, o is 1 or 2, r is 1 or 2, and p is 0.

In especially preferred embodiments, Y is chlorine, m is 0, n is 0, o is 1, r is 2, and p is 0.

A particularly useful 2-hydroxydiphenyl compound has the structure:

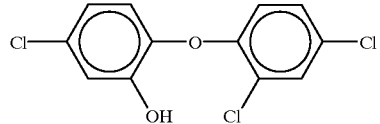

having the adopted name, triclosan, and available commercially under the tradename IRGASAN DP300, from Ciba Specialty Chemicals Corp., Greensboro, NC. Another useful 2-hydroxydiphenyl compound is 2,2'-dihydroxy-5,5'-dibromo-diphenyl ether.

(b) Phenol derivatives

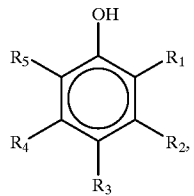

wherein $R_1$ is hydro, hydroxy, $C_1$–$C_4$ alkyl, chloro, nitro, phenyl, or benzyl; $R_2$ is hydro, hydroxy, $C_1$–$C_6$ alkyl, or halo; $R_3$ is hydro, $C_1$–$C_6$ alkyl, hydroxy, chloro, nitro, or a sulfur in the form of an alkali metal salt or ammonium salt; $R_4$ is hydro or methyl; and $R_5$ is hydro or nitro. Halo is bromo or, preferably, chloro.

Specific examples of phenol derivatives include, but are not limited to, chlorophenols (o-, m-, p-), 2,4- dichlorophenol, p-nitrophenol, picric acid, xylenol, p-chloro-m-xylenol, cresols (o-, m-, p-), p-chloro-m-cresol, pyrocatechol, resorcinol, 4-n-hexylresorcinol, pyrogallol, phloroglucin, carvacrol, thymol, p-chlorothymol, o-phenylphenol, o-benzylphenol, p-chloro-o-benzylphenol, phenol, 4-ethylphenol, and 4-phenolsulfonic acid. Other phenol derivatives are listed in WO 98/55096, incorporated herein by reference.

(c) Diphenyl Compounds

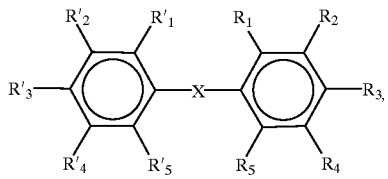

wherein X is sulfur or a methylene group, $R_1$ and $R'_1$ are hydroxy, and $R_2$, $R'_2$, $R_3$, $R'_3$, $R_4$, $R'_4$, $R_5$, and $R'_5$, independent of one another, are hydro or halo. Specific, nonlimiting examples of diphenyl compounds are hexachlorophene, tetrachlorophene, dichlorophene, 2,3-dihydroxy-5,5'-dichlorodiphenyl sulfide, 2,2'-dihydroxy-3, 3',5,5'-tetrachlorodiphenyl sulfide, 2,2'-dihydroxy-3,5',5,5', 6,6'-hexachlorodiphenyl sulfide, and 3,3'-dibromo-5,5'-dichloro-2,2'-dihydroxydiphenylamine. Other diphenyl compounds are listed in WO 98/55096, incorporated herein by reference.

Carrier

The carrier in the present composition comprises water.

Disinfecting Alcohol

Antibacterial compositions of the present invention contain about 1% to about 40%, by weight, of a disinfecting alcohol. Preferred embodiments contain about 2% to about 38%, by weight, of a disinfecting alcohol. Most preferred embodiments contain about 5% to about 30%, by weight, of a disinfecting alcohol.

As defined herein, the term "disinfecting alcohol" is a water-soluble alcohol containing one to six carbon atoms. Disinfecting alcohols include, but are not limited to, methanol, ethanol, propanol, and isopropyl alcohol.

Polyhydric Solvent

A polyhydric solvent, if present at all, is present in an amount of about 0.1% to about 50%, and preferably about 5% to about 50%, by weight of the composition. To achieve the full advantage of the present invention, the polyhydric solvent is present in an amount of about 10% to about 50% by weight of the composition. In contrast to a disinfecting alcohol, a polyhydric solvent contributes little, if at all, to the antibacterial efficacy of the present composition.

As defined herein, the term "polyhydric solvent" is a water-soluble organic compound containing two to six, and typically two or three, hydroxyl groups. The term "water-soluble" means that the polyhydric solvent has a water solubility of at least 0.1 g of polyhydric solvent per 100 g of water at 25° C. There is no upper limit to the water solubility of the polyhydric solvent, e.g., the polyhydric solvent and water can be soluble in all proportions.

The term "polyhydric solvent" therefore encompasses water-soluble diols, triols, and polyols. Specific examples of hydric solvents include, but are not limited to, ethylene glycol, propylene glycol, glycerol, diethylene glycol, dipropylene glycol, tripropylene glycol, hexylene glycol, butylene glycol, 1,2,6-hexanetriol, sorbitol, PEG-4, and similar polyhydroxy compounds.

Gelling Agent

The present antibacterial compositions also contain about 0.01% to about 5%, by weight, and preferably 0.10% to about 3%, by weight, of a gelling agent. To achieve the full advantage of the present invention, the antibacterial compositions contain about 0.25% to about 2.5%, by weight, of a gelling agent. The antibacterial compositions typically contain a sufficient amount of gelling agent such that the composition is a viscous liquid, gel, or semisolid that can be easily applied to, and rubbed on, the skin. Persons skilled in the art are aware of the type and amount of gelling agent to include in the composition to provide the desired composition viscosity or consistency.

The term "gelling agent" as used here and hereafter refers to a compound capable of increasing the viscosity of a water-based composition, or capable of converting a water-based composition to a gel or semisolid. The gelling agent, therefore, can be organic in nature, for example, a natural gum or a synthetic polymer, or can be inorganic in nature.

As previously stated, the present compositions are free of a surfactant. A surfactant is not intentionally added to a present antibacterial composition, but may be present in an amount of 0% to about 0.5%, by weight, because a surfactant may be present in a commercial form of a gelling agent to help dispense the gelling agent in water. A surfactant also may be present as an additive or by-product in other composition ingredients.

Surfactants are omitted from the present compositions to help avoid micelle formation, which in turn solubilize the active antibacterial compound and reduce its effectiveness. Similarly, preferred gelling agents are those that do not form micelles in particular, and do not complex or bind with the active antibacterial agents, or otherwise adversely effect the antibacterial properties of the antibacterial agent. Regardless of the identity of the gelling agent, the amount of gelling agents and other composition ingredients is selected such that the antibacterial agent is present in an amount of at least 25% of saturation, when measured at room temperature.

The following are nonlimiting examples of gelling agents that can be used in the present invention. In particular, the following compounds, both organic and inorganic, act primarily by thickening or gelling the aqueous portion of the composition:

acacia, acrylates/steareth-20 methacrylate copolymer, agar, algin, alginic acid, ammonium acrylate copolymers, ammonium alginate, ammonium chloride, ammonium sulfate, amylopectin, attapulgite, bentonite, C9–15 alcohols, calcium acetate, calcium alginate, calcium carrageenan, calcium chloride, caprylic alcohol, carbomer 910, carbomer 934, carbomer 934P, carbomer 940, carbomer 941, carboxymethyl hydroxyethylcellulose, carboxymethyl hydroxypropyl guar, carrageenan, cellulose, cellulose gum, cetearyl alcohol, cetyl alcohol, corn starch, damar, dextrin, dibenzylidine sorbitol, ethylene dihydrogenated tallowamide, ethylene dioleamide, ethylene distearamide, gelatin, guar gum, is guar hydroxypropyltrimonium chloride, hectorite, hyaluronic acid, hydrated silica, hydroxybutyl methylcellulose, hydroxyethylcellulose, hydroxyethyl ethylcellulose, hydroxyethyl stearamide-MIPA, hydroxypropylcellulose, hydroxypropyl guar, hydroxypropyl methylcellulose, isocetyl alcohol, isostearyl alcohol, karaya gum, kelp, lauryl alcohol, locust bean gum, magnesium aluminum silicate, magnesium silicate, magnesium trisilicate, methoxy PEG-22/dodecyl glycol copolymer, methylcellulose, microcrystalline cellulose, montmorillonite, myristyl alcohol, oat flour, oleyl alcohol, palm kernel alcohol, pectin, PEG-2M, PEG-5M, polyacrylic acid, polyvinyl alcohol, potassium alginate, potassium aluminum polyacrylate, potassium carrageenan, potassium chloride, potassium sulfate, potato starch, propylene glycol alginate, sodium acrylate/vinyl alcohol copolymer, sodium carboxymethyl dextran, sodium carrageenan, sodium cellulose sulfate, sodium chloride, sodium polymethacrylate, sodium silicoaluminate, sodium sulfate, stearalkonium bentonite, stearalkonium hectorite, stearyl alcohol, tallow alcohol, TEA-hydrochloride, tragacanth gum, tridecyl alcohol, tromethamine magnesium aluminum silicate, wheat flour, wheat starch, xanthan gum, and mixtures thereof.

The following additional nonlimiting examples of gelling agents act primarily by thickening the nonaqueous portion of the composition:

abietyl alcohol, acrylinoleic acid, aluminum behenate, aluminum caprylate, aluminum dilinoleate, aluminum distearate, aluminum isostearates/laurates/palmitates or stearates, aluminum isostearates/myristates, aluminum isostearates/palmitates, aluminum isostearates/stearates, aluminum lanolate, aluminum myristates/palmitates, aluminum stearate, aluminum stearates, aluminum tristearate, beeswax, behenamide, behenyl alcohol, butadiene/acrylonitrile copolymer, C29–70 acid, calcium behenate, calcium stearate, candelilla wax, carnauba, ceresin, cholesterol, cholesteryl hydroxystearate, coconut alcohol, copal, diglyceryl stearate malate, dihydroabietyl alcohol, dimethyl lauramine oleate, dodecanedioic acid/cetearyl alcohol/glycol copolymer, erucamide, ethylcellulose, glyceryl triacetyl hydroxystearate, glyceryl tri-acetyl ricinoleate, glycol dibehenate, glycol di-octanoate, glycol distearate, hexanediol distearate, hydrogenated C6–14 olefin polymers, hydrogenated castor oil, hydrogenated cottonseed oil, hydrogenated lard, hydrogenated menhaden oil, hydrogenated palm kernel glycerides, hydrogenated palm kernel oil, hydrogenated palm oil, hydrogenated polyisobutene, hydrogenated soybean oil, hydrogenated tallow amide, hydrogenated tallow glyceride, hydrogenated vegetable glyceride, hydrogenated vegetable glycerides, hydrogenated vegetable oil, hydroxypropylcellulose, isobutylene/isoprene copolymer, isocetyl stearoyl stearate, Japan wax, jojoba wax, lanolin alcohol, lauramide, methyl dehydroabietate, methyl hydrogenated rosinate, methyl rosinate, methylstyrene/vinyltoluene copolymer, microcrystalline wax, montan acid wax, montan wax, myristyleicosanol, myristyloctadecanol, octadecene/maleic anhydride copolymer, octyldodecyl stearoyl stearate, oleamide, oleostearine, ouricury wax, oxidized polyethylene, ozokerite, palm kernel alcohol, paraffin, pentaerythrityl hydrogenated rosinate, pentaerythrityl rosinate, pentaerythrityl tetraabietate, pentaerythrityl tetrabehenate, pentaerythrityl tetraoctanoate, pentaerythrityl tetraoleate, pentaerythrityl tetrastearate, phthalic anhydride/glycerin/glycidyl decanoate copolymer, phthalic/trimellitic/glycols copolymer, polybutene, polybutylene terephthalate, polydipentene, polyethylene, polyisobutene, polyisoprene, polyvinyl butyral, polyvinyl laurate, propylene glycol dicaprylate, propylene glycol dicocoate, propylene glycol diisononanoate, propylene glycol dilaurate, propylene glycol dipelargonate, propylene glycol distearate, propylene glycol diundecanoate, PVP/eicosene copolymer, PVP/hexadecene copolymer, rice bran wax, stearalkonium bentonite, stearalkonium hectorite, stearamide, stearamide DEA-distearate, stearamide DIBA-stearate, stearamide MEA-stearate, stearone, stearyl alcohol, stearyl erucamide, stearyl stearate, stearyl stearoyl stearate, synthetic beeswax, synthetic wax, trihydroxystearin, triisononanoin, triisostearin, triisononanoin, triisostearin, tri-isostearyl trilinoleate, trilaurin, trilinoleic acid, trilinolein, trimyristin, triolein, tripalmitin, tristearin, zinc laurate, zinc myristate, zinc neodecanoate, zinc rosinate, zinc stearate, and mixtures thereof.

Hydrotrope

The hydrotrope, if present at all, is present in an amount of about 0.1% to about 30%, and preferably about 0.5% to about 25%, by weight of the composition. To achieve the full advantage of the present invention, the hydrotrope is present in an amount of about 1% to about 20%, by weight of the composition.

A hydrotrope is a compound that has the ability to enhance the water solubility of other compounds. A hydrotrope lacks surfactant properties, and typically is a short-chain alkyl aryl sulfonate. Specific examples of hydrotropes include, but are not limited to, sodium cumene sulfonate, ammonium cumene sulfonate, ammonium xylene sulfonate, potassium toluene sulfonate, sodium toluene sulfonate, sodium xylene sulfonate, toluene sulfonic acid, and xylene sulfonic acid. Other useful hydrotropes include sodium polynaphthalene sulfonate, sodium polystyrene sulfonate, sodium methyl naphthalene sulfonate, and disodium succinate.

Optional Ingredients

An antibacterial composition of the present invention also can contain optional ingredients well known to persons skilled in the art. For example, the composition can contain other optional ingredients, such as dyes and fragrances, that are present in a sufficient amount to perform their intended function and do not adversely affect the antibacterial efficacy of the composition. Such optional ingredients typically are present, individually, from 0% to about 5%, by weight, of the composition, and, collectively, from 0% to about 20%, by weight, of the composition.

Classes of optional ingredients include, but are not limited to, dyes, fragrances, pH adjusters, buffering agents, antioxidants, skin conditioners and protectants, chelating agents, opacifiers, vitamins, and similar classes of optional ingredients known to persons skilled in the art.

Specific classes of optional ingredients include inorganic phosphates, sulfates, and carbonates as buffering agents; vitamins A, E, and C as vitamins; polyamino acids and salts, like EDTA, and phosphates as chelating agents; and acids and bases as pH adjusters.

Examples of preferred classes of basic pH adjusters are ammonia; mono-, di-, and tri-alkyl amines; mono-, di-, and tri-alkanolamines; alkali metal and alkaline earth metal hydroxides; and mixtures thereof. However, the identity of the basic pH adjuster is not limited, and any basic pH adjuster known in the art can be used. Specific, nonlimiting examples of basic pH adjusters are ammonia; sodium, potassium, and lithium hydroxide; monoethanolamine; triethylamine; isopropanolamine; diethanolamine; and triethanolamine.

Examples of preferred classes of acidic pH adjusters are the mineral acids and polycarboxylic acids. Nonlimiting examples of mineral acids are hydrochloric acid, nitric acid, phosphoric acid, and sulfuric acid. Nonlimiting examples of polycarboxylic acids are citric acid, glycolic acid, and lactic acid. The identity of the acidic pH adjuster is not limited and any acidic pH adjuster known in the art, alone or in combination, can be used.

Examples of skin conditioners, include emollients, such as, cetyl myristate, glyceryl dioleate, isopropyl myristate, lanolin, methyl laurate, PPG-9 laurate, soy stearyl, octyl palmitate, and PPG-5 lanoate, for example. The skin conditioner also can be a humectant, for example, glucamine and pyridoxine glycol, for example. Occlusive skin conditioners, for example, aluminum lanolate, corn oil, methicone, coconut oil, stearyl stearate, phenyl trimethicone, trimyristin, olive oil, and synthetic wax, also can be used. Combinations of the classes of skin conditioners, in addition to miscellaneous skin conditioners known to persons skilled in the art, alone or in combination can be used. Nonlimiting examples of miscellaneous skin conditioners include aloe, cholesterol, cystine, keratin, lecithin, egg yolk, glycine, PPG-12, retinol, salicylic acid, orotic acid, vegetable oil, and soluble animal collagen. The skin conditioners can be used alone, or in combination with a skin protectant, like petroleum, cocoa butter, calamine, and kaolin, for example. A skin protectant also can be used alone. Additional examples of skin conditioners and protectants can be found in "CTFA Cosmetic Ingredient Handbook," J. M. Nikitakis, ed., The Cosmetic, Toiletry and Fragrance Association, Inc., Washington, D.C. (1988) (hereafter CTFA Handbook), pages 79–85, incorporated herein by reference.

Antibacterial compositions of the present invention comprising an active antibacterial agent, a disinfecting alcohol, and a hydrotrope exhibit a rapid bacteria kill. The solvent and hydrotrope assist in solubilizing the antibacterial agent. Accordingly, at least 25% saturation of the antibacterial agent in the composition can be achieved even in the absence of a surfactant.

The antibacterial compositions of the present invention do not rely upon a high concentration of disinfecting alcohol, or a low pH or a high pH, to provide a rapid reduction in bacterial populations. Antibacterial compositions of the present invention can have a pH of about 4 to about 9, but at the two extremes of this pH range, the compositions can be irritating to the skin or damaging to other surfaces contacted by the composition. Accordingly, antibacterial compositions of the present invention preferably have a pH of about to about 8, and more preferably about 6 to about 8. To achieve the full advantage of the present invention, the antibacterial compositions have a pH of about 6.5 to about 7.5.

To demonstrate the new and unexpected results provided by the antibacterial compositions of the present invention, the following Examples and Comparative Examples were prepared, and the ability of the compositions to control Gram positive and Gram negative bacteria was determined. The weight percentage listed in each of the following examples represents the actual (active) weight amount of each ingredient present in the composition, except where noted. The compositions were prepared by blending the ingredients, as understood by those skilled in the art and as described below.

The following materials were used as ingredients in the examples. The source of each ingredient, and its abbreviation, are summarized below:

a) Dipropylene glycol (DPG), Dow Chemical Co., Midland, Mich., b) p-Chloro-m-xylenol (PCMX), NIPACIDE PX-R, Nipa Inc., Wilmington, Del. (about 100% active), c) Glyceryl polymethacrylate and propylene glycol (LUBRAGEL DV), International Speciality Products, Wayne, N.J. (about 46% active), d) CARBOPOL ULTREZ 10 (ULTREZ 10), crosslinked polyacrylic acid, BF Goodrich Specialty Chemicals, Cleveland, Ohio (about 98% active), e) Isopropanol (IPA), Fisher Scientific, Pittsburgh, PA, 2-Propanol, HPLC Grade A 451–4, f) Liquid Perfume (PF), g) Diisopropylamine, Air Products and Chemicals, Allentown, Pa. (about 100% active), h) Propylene glycol (PG), Dow Chemical Co., USP Grade (active level=99.96%), i) LAPONITE XLG (lithium magnesium silicate, synthetic smectite clay), Southern Clay Products, Gonzales, Tex. (about 99% active), j) CELQUAT CS230M (Polyquaternium 10), National Starch and Chemical Company, Bridgewater, N.J. (about 92% active), k) Sodium xylene sulfonate (SXS), Stepan Chemical Co., STEPANATE SXS (active level=40–42%), l) Triclosan (TCS), IRGASAN DP-300, Ciba Specialty Chemicals Corp., Greensboro, NC (GC assay on lots used=99.8–99.9% active TCS; mp=56.0–58.0 C.), m) Polypropylene glycol-9 (PPG-9), Polyglycol P425, Dow Chemical Company, Midland, Michigan (about 100% active), n) Water—distilled or deionized, o) Ethanol (Denatured Ethyl Alcohol 40B), Gold Shield, Hayward, California (about 100% active).

The following methods were used in the preparation and testing of the examples:

a) Determination of Rapid Germicidal (Time Kill) Activity of Antibacterial Products. The activity of antibacterial compositions was measured by the time kill method, whereby the survival of challenged organisms exposed to an antibacterial test composition is determined as a function of time. In this test, a diluted aliquot of the composition is brought into contact with a known population of test bacteria for a specified time period at a specified temperature. The test composition is neutralized at the end of the time period, which arrests the antibacterial activity of the composition. The percent or, alternatively, log reduction from the original bacteria population is calculated. In general, the time kill method is known to those skilled in the art.

The composition can be tested at any concentration from 0–100%. The choice of which concentration to use is at the discretion of the investigator, and suitable concentrations are readily determined by those skilled in the art. For example, viscous samples usually are tested at 50% dilution, whereas nonviscous samples are not diluted. The test sample is placed in a sterile 250 ml (milliliter) beaker equipped with a magnetic stirring bar and the sample volume is brought to 100 ml, if needed, with sterile deionized water. All testing is performed in triplicate, the results are combined, and the average log reduction is reported.

The choice of contact time period also is at the discretion of the investigator. Any contact time period can be chosen. Typical contact times range from 15 seconds to 5 minutes, with 30 seconds and 1 minute being typical contact times. The contact temperature also can be any temperature, typically room temperature, or about 25 degrees Celsius.

The bacterial suspension, or test inoculum, is prepared by growing a bacterial culture on any appropriate solid media (e.g., agar). The bacterial population then is washed from the agar with sterile physiological saline and the population of the bacterial suspension is adjusted to about $10^8$ colony forming units per ml (cfu/ml).

The table below lists the test bacterial cultures used in the following tests and includes the name of the bacteria, the ATCC (American Type Culture Collection) identification number, and the abbreviation for the name of the organism used hereafter.

| Organism Name | ATCC # | Abbreviation |
|---|---|---|
| Staphylococcus aureus | 6538 | S. aureus |
| Escherichia coli | 11229 | E. coli |
| Klebsiella pneumoniae | 10031 | K. pneum. |
| Salmonella choleraesuis | 10708 | S. choler. |

*S. aureus* is a Gram positive bacteria, whereas *E. coli*, *K. pneum*, and *S. choler.* are Gram negative bacteria.

The beaker containing the test composition is placed in a water bath (if constant temperature is desired), or placed on a magnetic stirrer (if ambient laboratory temperature is desired). The sample then is inoculated with 1.0 ml of the test bacteria suspension. The inoculum is stirred with the test composition for the predetermined contact time. When the contact time expires, 1.0 ml of the test composition/bacteria mixture is transferred into 9.0 ml of Tryptone-Histidine-Tween Neutralizer Solution (THT). Decimal dilutions to a countable range then are made. The dilutions can differ for different organisms. Plate selected dilutions in triplicate on TSA+plates (TSA+is Trypticase Soy Agar with Lecithin and Polysorbate 80). The plates then are incubated for 25±2 hours, and the colonies are counted for the number of survivors and the calculation of percent or log reduction. The control count (numbers control) is determined by conducting the procedure as described above with the exception that THT is used in place of the test composition. The plate counts are converted to cfu/ml for the numbers control and samples, respectively, by standard microbiological methods.

The log reduction is calculated using the formula

Log reduction=$\log_{10}$(numbers control)–$\log_{10}$(test sample survivors)

The following table correlates percent reduction in bacteria population to log reduction:

| % Reduction | Log Reduction |
|---|---|
| 90 | 1 |
| 99 | 2 |
| 99.9 | 3 |
| 99.99 | 4 |
| 99.999 | 5 | b) Preparation of saturated solutions of TCS in water: A four liter flask was equipped with a 3-inch magnetic stir bar and charged with approximately 7.5 grams (g) TCS and 3 liters (L) of water. The flask then was placed in a water bath, stirred, and heated (40–45° C.) for at least 8 hours. The flask containing the resulting TCS/water suspension was removed from the water bath, and the warm suspension filtered through a Coors #32-H porcelain BUchner funnel equipped with Whatman #40 (5.5 centimeters) filter paper. The filtering assembly was attached to a two liter vacuum filter flask, and filtration was conducted in batches. The filtrate then was transferred to another four liter flask and allowed to cool. Typically, fine needles of TCS crystals formed after the filtrate was stored at room temperature for a few days.

For some time kill studies, the TCS solution was refiltered at room temperature before use in the study. For other time kill studies, a small amount of crystalline TCS was allowed to remain in the test container to ensure saturation in the event of a temperature change. It was assumed that TCS crystals present in the time kill test vessel would not affect test results because crystalline TCS is unavailable to act on the bacteria (i.e., is not solubilized).

To determine the concentration of TCS in the water solutions, filtered samples (in triplicate) were analyzed by HPLC. The apparatus used to filter the solutions was a Whatman AUTOVIAL®, with 0.45 µm (micrometer) PTFE membrane and glass microfiber prefilter, cat. No. AV125UORG. TCS concentrations were calculated using a linear regression line fit (Microsoft EXCEL® software) to TCS/IPA standards included on the same HPLC run.

c) Preparation of compositions containing TCS and a solvent or solvent/hydrotrope combination: TCS first was dissolved in the solvent used in the composition, i.e., a disinfecting alcohol and/or a polyhydric solvent. Water then was added to the TCS/solvent composition, followed by the addition of about 1 mg (milligram) of TCS seed crystals, and the resulting mixture was allowed to stand at about 20° C. to crystallize. In compositions containing a solvent, hydrotrope, and surfactant, the TCS was dissolved in the solvent as above, and then the hydrotrope and surfactant were added to the TCS/solvent solution. The resulting mixture then was diluted to the batch total with water. Adjustment of pH also was performed, if required. The mixture was stirred at room temperature for about an hour, seed TCS was added, and the mixture allowed to stand and crystallize as above. The determination of the TCS saturation point described above also was used (i.e., halving surfactant concentrations). Methods similar to the above for determination of maximum additive concentration have been described in the literature. For example, P. H. Elworthy et al., "Solubilization by surface-active agents and its application in chemistry and biological sciences," Chapman and Hall, Ltd., London, pp. 62–65 (1968), describes determination of concentrations near saturation by observing turbidity of the mixture. A similar technique was used by observing the sample at right angles with a high-intensity light from a small flashlight equipped with a beam focusing attachment (i.e., MINI MAGLITE® AA, MAG Instruments, California, USA). This method also was used with solutions very near to saturation to enhance observation of small amounts of crystals formed on the bottom of containers.

Table 2 summarizes the results of time kill tests performed on TCS/water compositions. Two series of results, I and II, demonstrate the effect of % saturation in TCS/water compositions, i.e., that within a given test series, reduction in % saturation produces a concomitant reduction in time kill efficacy.

TABLE 2

Time Kill Results for Saturated TCS/Water Compositions

| Sample | | TCS (g/mL) (by HPLC) | LOG REDUCTION | | | | | | | |
|---|---|---|---|---|---|---|---|---|---|---|
| | | | S. aureus | | E. coli | | K. pneum. | | S. chol. | |
| | | | 1 min/or t | 5 min. | 1 min/or t | 5 min | 1 min/or t | 5 min | 1 min/or t | 5 min |
| I | 100% sat'd. | $9.3 \times 10^{-7}$ | 1.07/15s | >3.91 | 0.44/15s | >4.06 | 0.32/15s | >4.00 | | |
| | 50% sat'd. | $3.9 \times 10^{-7}$ | 0.03/15s | 1.71 | 0.13/15s | 1.15 | 0.21/15s | 2.76 | | |
| | 10% sat'd. | $6.7 \times 10^{-8}$ | 0.03/15s | 0.02 | 0.06/15s | 0.08 | 0/15s | 0.14 | | |
| II | 100% sat'd. | $9.6 \times 10^{-6}$ | 3.93 | | 1.76 | | 2.85 | | 2.15 | |
| | 50% sat'd. | $4.9 \times 10^{-6}$ | 0.24 | | 0.26 | | 0.35 | | 1.28 | |

Comparing the data in Tables 2 and 3 shows that at the very lowest concentration of TCS (i.e., 5 to 10 ppm), the efficacy of time kill is reduced compared to samples containing higher levels of TCS. For example, a sample in Table 2 containing 0.93 ppm TCS has a log reduction of 0.44 after 15 seconds vs. *E. coli*, whereas a sample in Table 3 containing 484 ppm TCS had a log reduction of 4.13 after 15 seconds vs. the same organism. This effect is more apparent at shorter-contact time periods. Another example, in more complex compositions is illustrated in samples in Table 3, i.e., 50 ppm TCS (est.)/10%PG/5%SXS vs. (448 ppm TCS (est.)/20%PG/10%SXS). The sample with the higher TCS concentration showed at least a log improvement in bacterial reduction after 1 minute. The data in Table 3 also show differences in efficacy when different solvents/hydrotropes are used with approximately the same TCS concentrations.

TABLE 3

TCS in Solvent and/or Hydrotrope Systems

| TCS (ppm) | Solvent/ Hydrotrope | log reduction/ time[1] | log reduction at 1 min. | log reduction/ time[1] | log reduction at 1 min. |
|---|---|---|---|---|---|
| | | S. aureus | | E. coli | |
| 112 (est) | 17% IPA | | >4.42 | | >3.56 |
| 0 | 17% IPA | | 0.42 | | −0.24 |
| 110 (est) | 23.85% PG | | >4.39 | | 2.37 |
| 342 | 40.01% PG | 4.97/30 | >5.17 | 4.29/30 | >4.67 |
| 484 | 41.86% PG | >3.46/15 | >3.46 | 4.13/15 | >4.38 |
| 510 | 42.53% PG | >5.17/30 | >5.17 | 4.47/30 | >4.67 |
| 723 | 44.20% PG | >3.46/15 | >3.46 | >4.38/15 | >4.38 |
| 603 | 45.05% PG | >4.49/15 | >4.49 | 4.21/15 | >4.65 |
| 895 | 47.52% PG | >5.17/30 | >5.17 | 4.42/30 | >4.67 |
| 1385 | 50.00% PG | >4.49/15 | >4.49 | 4.45/15 | >4.65 |
| 0 | 50.00% PG | 0.15/15 | 0.13 | 0.25/15 | 0.26 |
| 0 | 75.00% PG | 1.20/15 | 2.35 | 0.35/15 | 1.73 |
| 63 | 5% SXS | | >4.43 | | 0.96 |
| 0 | 5% SXS | | 0.33 | | −0.15 |
| 57 | 5% SCS | | 3.64 | | 0.80 |
| 0 | 5% SCS | | −0.05 | | −0.11 |
| 448 (est) | 20% PG/ 10% SXS | >4.14/30 | >4.14 | >5.25/30 | >5.25 |
| 0 | 20% PG/ 10% SXS | 0.05/30 | 0.05 | 1.16/30 | 1.35 |
| 50 (est) | 10% PG/ 5% SXS | | 3.42 | | 3.18 |
| 0 | 10% PG/ 5% SXS | | 0.05 | | 0.35 |
| 50 (est) | 10% PG/ 5% SCS | | 0.59 | | 4.96 |
| 0 | 10% PG/ 5% SCS | | −0.03 | | 0.96 |
| 502 | 14.5% DPG/ | >3.63/30 | >3.63 | >4.44/30 | >4.44 |

TABLE 3-continued

TCS in Solvent and/or Hydrotrope Systems

| TCS (ppm) | Solvent/ Hydrotrope | log reduction/ time[1] | log reduction at 1 min. | log reduction/ time[1] | log reduction at 1 min. |
|---|---|---|---|---|---|
| (est) | 10% SXS | | | | |
| 0 | 14.5% DPG/ 10% SXS | 0.03.30 | 0.04 | 0.26/30 | 0.17 |
| | | K. pneum. | | S. chol. | |
| 112 (est) | 17% IPA | | >4.11 | | >3.79 |
| 0 | 17% IPA | | 0.89 | | 1.23 |
| 110 (est) | 23.85% PG | | | | |
| 342 | 40.01% PG | 4.33/30 | 5.29 | 2.52/30 | 3.51 |
| 484 | 41.86% PG | 2.96/15 | >3.44 | 1.14/15 | 2.31 |
| 510 | 42.53% PG | 4.61/30 | >5.64 | 2.55/30 | 3.79 |
| 723 | 44.20% PG | >3.44/15 | >3.44 | 1.29/15 | 2.59 |
| 603 | 45.05% PG | 2.60/15 | 4.79 | 1.79/15 | >4.50 |
| 895 | 47.52% PG | 5.26/30 | >5.64 | 2.92/30 | 4.33 |
| 1385 | 50.00% PG | 3.26/15 | >5.04 | 2.69/15 | >4.59 |
| 0 | 50.00% PG | 0.54/15 | 0.63 | 0.17/15 | 0.24 |
| 0 | 75.00% PG | 1.98/15 | >3.44 | 1.34/15 | 3.56 |
| 63 | 5% SXS | | | | |
| 0 | 5% SXS | | | | |
| 57 | 5% SCS | | | | |
| 0 | 5% SCS | | | | |
| 448 (est) | 20% PG/ 10% SXS | >4.32/30 | >4.32 | 3.17/30 | >3.68 |
| 0 | 20% PG/ 10% SXS | 0.22/30 | 0.37 | 0.25/30 | 1.29 |
| 50 (est) | 10% PG/ 5% SXS | | | | |
| 0 | 10% PG/ 5% SXS | | | | |
| 50 (est) | 10% PG/ 5% SCS | | | | |
| 0 | 10% PG/ 5% SCS | | | | |
| 502 (est) | 14.5% DPG/ 10% SXS | >4.14/30 | >4.14 | >4.14/30 | >4.14 |
| 0 | 14.5% DPG/ 10% SXS | 0.34/30 | 0.39 | 0.36/30 | 0.47 |

[1]time in seconds.

EXAMPLE 1

In this example, a polyhydric solvent, (i.e., propylene glycol (PG)) was used to solubilize triclosan in an aqueous carrier. No hydrotrope was present. Composition A-3 contained 0.0895% by weight triclosan, 47.5% aqueous PG, and the balance being water. Composition A-3 was 100% saturated with triclosan. Test composition A-4 was a "placebo" consisting of 47.5% PG, by weight, and the balance water. This example illustrates the advantages of including TCS in the composition. In particular, it was observed that an excellent broad spectrum activity can be achieved in a contact time of 30 seconds. This example further demonstrates that the antibacterial activity of a present composition is unambiguously attributable to the presence of the antibacterial agent.

| | | | Log Reduction at 30 seconds (time kill) | | | |
|---|---|---|---|---|---|---|
| Product | Triclosan % | % Saturation | S. aureus | E. coli | K. pneum. | S. chol. |
| A-3 | 0.0895 | 100 | >5.17 | 4.42 | 5.26 | 2.92 |
| A-4 | 0.0 | 0 | 0.15 | 0.25 | 0.54 | 0.17 |

EXAMPLE 2

This example illustrates that composition of the present invention provide an acceptable sanitization efficacy even though the compositions contain a relatively low concentration of disinfecting alcohol. Examples B-1, B-3, and B-5 contain 0.15%, by weight, triclosan, at 100% saturation. Examples B-2, B-4, and B-6 are comparative examples containing 0% triclosan.

| | % (by weight) | | | | | |
|---|---|---|---|---|---|---|
| Ingredient | B-1 | B-2 | B-3 | B-4 | B-5 | B-6 |
| Triclosan | 0.15 | 0.0 | 0.15 | 0.0 | 0.15 | 0.0 |
| Ethanol | 38 | 38.0 | 28.0 | 28.0 | — | — |
| Dipropylene Glycol | — | — | 11.18 | 11.18 | 40.0 | 40.0 |
| ULTREZ 10[1)] | 0.3 | 0.3 | 0.3 | 0.3 | 0.3 | 0.3 |
| Diisopropylamine | 0.05 | 0.05 | 0.05 | 0.05 | 0.05 | 0.05 |
| Perfume | 0.04 | 0.04 | 0.04 | 0.04 | 0.04 | 0.04 |
| Water | Balance | Balance | Balance | Balance | Balance | Balance |

[1)]added "as is"

The following table summarizes the results of a time kill test at 15 seconds.

| | Log Reductions at 15 seconds | | | |
|---|---|---|---|---|
| Example | S. aureus | E. coli | K. pneum. | S. chol. |
| E-1 | >4.61 | >4.78 | >4.51 | >4.49 |
| B-2 | >4.61 | >4.78 | >4.51 | >4.49 |
| B-3 | >4.00 | >4.44 | >4.20 | >3.92 |
| B-4 | 2.50 | 1.20 | >4.20 | >3.92 |
| B-5 | >4.39 | 3.29 | 1.37 | 1.30 |
| B-6 | 0.10 | 0.0 | 0.35 | 0.34 |

These results show that acceptable sanitization efficacy is achieved, even with reduced levels of disinfecting alcohol and other polyhydric solvents. Furthermore, the compositions of the present invention provide a persistent antibacterial benefit because of the nonvolatile nature of the active ingredient, triclosan, whereas presently marketed compositions do not provide a persistent antibacterial activity.

In particular, Examples B-3 through B-6 demonstrate that the rapid antibacterial activity of the present compositions is attributable mainly to the antibacterial agent, e.g., triclosan, as opposed to a disinfecting alcohol. This is in contrast to prior art disclosures. For example, composition B-3 contains only 28% ethanol, yet exhibits excellent broad-spectrum antibacterial activity at 15 seconds. Composition B-5 contains no alcohol, yet exhibits excellent antibacterial activity against S. aureus and E. coli. Prior art teachings rely on a high alcohol concentration (i.e., >40%) to achieve a fast, broad-spectrum antibacterial activity.

EXAMPLE 3

The following compositions 3-A through 3-D were prepared to demonstrate the superior germ kill provided by compositions of the present invention compared to control compositions (i.e., compositions free of an antibacterial agent), even when very low amounts of disinfecting alcohol are present. Compositions 3A–3D were prepared using standard mixing techniques known in the art. Table 4 below lists the composition ingredients. Table 5 below summarizes the antibacterial efficacy of compositions 3-A through 3-D, as measured in a time kill test.

TABLE 4

| | % by weight (as active substance) | | | | |
|---|---|---|---|---|---|
| Composition | TCS | Ethanol | PPG-9 | DPG | Water |
| 3-A (control) | 0 | 25.86 | 11.5 | — | Balance |
| 3-B | 0.10 | 25.86 | 11.5 | — | Balance |
| 3-C (control) | 0 | 23.0 | — | 11.18 | Balance |
| 3-D | 0.10 | 23.0 | — | 11.18 | Balance |

TABLE 5

| | Log reduction @ 15 sec/30 sec | | | |
|---|---|---|---|---|
| Composition | S. aureus | E. coli | K. pneum. | S. chol. |
| 3-A | 0.55/1.73 | 0.18/0.43 | 1.15/0.71 | 2.51/4.24 |
| 3-B | 3.27/>4.43 | 3.75/>4.51 | 1.33/3.10 | 4.09/4.34 |
| 3-C | 0.01/0.0 | 0.17/0.12 | 0.4/0.11 | 0.18/0.17 |
| 3-D | >4.43/>4.43 | 3.20/3.4.8 | 3.19/4.03 | 2.86/3.99 |

Example 3 illustrates the surprisingly high efficacy of compositions of the present invention (3-B and 3-D), wherein high log reductions are observed against both Gram positive and Gram negative bacteria, even for compositions containing less than 26% ethanol. The results are in contrast to compositions described in prior disclosures, wherein high alcohol concentrations (i.e., greater than about 40%) are relied upon to achieve a high, broad spectrum antibacterial activity.

EXAMPLE 4

Example 4 shows that compositions of the present invention provide excellent, broad spectrum antibacterial activity, even at further reduced alcohol concentrations. Accordingly, composition 4-A containing 0.15% TCS, 11.18% ethanol, 25.71% DPG, the balance being water (as weight percent of active compounds), was prepared. For comparison, an identical control composition 4-B was prepared, except composition 4-B was free of TCS. The following table summarizes the results of antibacterial efficacy of compositions 4-A and 4-B by time kill tests.

| | Log reduction @ 15 sec/30 sec | | | |
|---|---|---|---|---|
| Composition | S. aureus | E. coli | K. pneum. | S. chol. |
| 4-A | 4.54/>4.69 | >4.78/>4.78 | 3.63/>4.11 | 1.12/1.31 |
| 4-B | 0.88/0.97 | 0.36/0.37 | 0.0/0.0 | 0.0/0.0 |

Example 4 further demonstrates that the concentration of alcohol in the present compositions can be reduced to very low levels without sacrificing antibacterial activity. Accordingly, compositions that provide excellent antibacterial efficacy, and that do not dry the skin, can be prepared. Prior compositions that relied on a high alcohol concentration-for antibacterial activity dried the skin, and often caused skin irritation.

EXAMPLE 5

Example 5 demonstrates that highly effective compositions of the present invention can incorporate p-chloro-m-xylenol (PCMX) as the antibacterial active agent. Composition 5-A was prepared by admixing 0.1% PCMX, 13.42% ethanol, and the balance water (as weight percent of active compounds). The antibacterial efficacy of composition 5-A was evaluated by a time kill test and exhibited log reductions against S. aureus, E. coli, K. pneum., and S. chol., at 30 seconds contact time, of 4.16, >4.34, 3.99, and >4.04, respectively. Thus, composition 5-A is a highly effective antibacterial composition, even though the composition contained a very low concentration of ethanol.

EXAMPLE 6

Example 6 illustrates a composition of the present invention containing a cationic gelling agent, CELQUAT CS-230M. Composition 6-A was prepared by admixing 0.15% TCS, 28% ethanol, 11.18% DPG, and 2% CELQUAT CS-230M, and the balance was water (as weight percent of active compounds, except CELQUAT, which is "as-is"). The antibacterial efficacy of composition 6-A was evaluated by a time kill test. Composition 6-A demonstrated the following log reductions against S. aureus, E. coli, K. pneum., and S. chol., at 30 seconds contact time of >3.83, 4.33, >4.43, and >3.55, respectively. Thus, composition 6-A is a highly effective antibacterial composition, even though the composition contained a very low concentration of ethanol.

EXAMPLE 7

Compositions of the present invention can contain a wide variety of gelling agents, hydric solvents, and antibacterial active agents, illustrated by the following examples. In Table 6 below, all weight percentages are as active material, except where indicated by a "*," which indicates an "as-is" weight. The compositions were prepared by mixing and gel preparation techniques well known to persons skilled in the art. The compositions exhibited acceptable clarity, stability, and performance.

TABLE 6

| Ingredient | A | B | C | D | E | F | G | H | I | J | K | L | M | N | O | P | Q | R | S | T |
|---|---|---|---|---|---|---|---|---|---|---|---|---|---|---|---|---|---|---|---|---|
| TCS | 0.1 | 0.1 | 0.1 | 0.1 | 0.1 | 0.1 | 0.1 | 0.15 | 0.1 | 0.11 | 0.1 | 0.1 | 0.1 | 0.1 | 0.1 | 0.1 | 0.1 | | | |
| Deionized Water | qs | qs | qs | qs | qs | qs | qs | qs | qs | qs | qs | qs | qs | qs | qs | qs | qs | qs | qs | qs |
| LUBRAGEL DV* | 15 | 15 | 10 | 10 | 10 | 10 | 10 | 10 | 10 | | | | | | | | | | | |
| IPA | 18.5 | | | | | | | | | 24.93 | | 18.5 | 18.5 | | | | | | | |
| Propylene Glycol | 14 | 14 | 14 | | | | | | | | 44.2 | 14 | 14 | | | | | | | |
| Ethanol | | 23 | 23 | 23 | | 23 | | 34.25 | 23 | | | | | 23 | 35 | 28 | 28 | 23 | 28.07 | 4.1 |
| PPG-9 | | | | 11.5 | 36 | | | | | | | | | | | | | 14.14 | 11.16 | 7.26 |
| DPG | | | | | | 11.18 | 35 | | 11.18 | | | | | 11.18 | | 11.18 | 11.18 | | | |
| Perfume | | | | | | | | | 0.5 | | | | | | 0.04 | 0.2 | 0.04 | | | |
| LAPONITE XLG* | | | | | | | | | | | 1.5 | 1.5 | 1.5 | 2 | | | | | | |
| CELQUAT CS 230M* | | | | | | | | | | | | | | | 2.5 | 2 | 2 | 2 | | |
| PCMX | | | | | | | | | | | | | | | | | | 0.1 | 0.15 | 0.1 |
| ULTREZ 10* | | | | | | | | | | | | | | | | | | 0.3 | 0.3 | 0.3 |
| Diisopropylamine | | | | | | | | | | | | | | | | | | 0.05 | 0.05 | 0.05 |

Obviously, many modifications and variations of the invention as hereinbefore set forth can be made without departing from the spirit and scope thereof, and, therefore, only such limitations should be imposed as are indicated by the appended claims.

What is claimed is:

1. An antimicrobial composition comprising:
   (a) about 0.05% to about 5%, by weight, of a phenolic antibacterial agent;
   (b) about 1% to about 40%, by weight, of a disinfecting alcohol;
   (c) about 0.1% to about 5%, by weight, of a gelling agent; and
   (d) water,
   wherein the composition is free of a surfactant,
   and wherein the antibacterial agent is present in the composition in an amount of at least 50% of saturationconcentration, when measured at room temperature.

2. The composition of claim 1 having a log reduction against Gram positive bacteria of at least 2 after 30 seconds of contact, as measured against S. aureus, and a log reduction against Gram negative bacteria of at least 2.5 after 30 seconds of contact, as measured against E. coli.

3. The composition of claim 1 wherein the antibacterial agent is present in an amount of at least 75% of saturation concentration.

4. The composition of claim 1 wherein the antibacterial agent is present in an amount of at least 95% of saturation concentration.

5. The composition of claim 1 comprising about 0.1% to about 4% by weight, of the phenolic antibacterial agent.

6. The composition of claim 1 comprising about 0.25% to about 2% by weight, of the phenolic antibacterial agent.

7. The composition of claim 1 wherein the phenolic antibacterial agent is selected from the group consisting of:

(a) a 2-hydroxydiphenyl compound having the structure

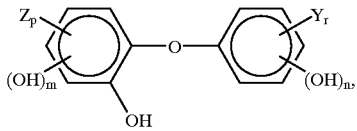

wherein Y is chlorine or bromine, Z is $SO_2H$, $NO_2$, or $C_1$–$C_4$ alkyl, r is 0 to 3, o is 0 to 3, p is 0 or 1, m is 0 or 1, and n is 0 or 1;

(b) a phenol derivative having the structure

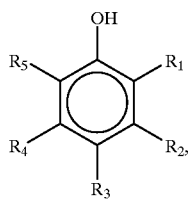

wherein $R_1$ is hydro, hydroxy, $C_1$–$C_4$ alkyl, chloro, nitro, phenyl, or benzyl; $R_2$ is hydro, hydroxy, $C_1$–$C_6$ alkyl, or halo; $R_3$ is hydro, $C_1$–$C_6$ alkyl, hydroxy, chloro, nitro, or a sulfur in the form of an alkali metal salt or ammonium salt; $R_4$ is hydro or methyl, and $R_5$ is hydro or nitro;

(c) a diphenyl compound having the structure

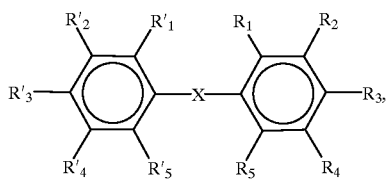

wherein X is sulfur or a methylene group, $R_1$ and $R'_1$ are hydroxy, and $R_2$, $R'_2$, $R_3$, $R'_3$, $R_4$, $R'_4$, $R_5$, and $R'_5$, independent of one another, are hydro or halo; and (d) mixtures thereof.

8. The composition of claim 7 wherein the antibacterial agent comprises triclosan, p-chloro-m-xylenol, or mixtures thereof.

9. The composition of claim 1 wherein the disinfecting alcohol is present in an amount of about 2% to about 35%, by weight.

10. The composition of claim 1 wherein the disinfecting alcohol is present in an amount of about 5% to about 30%, by weight.

11. The composition of claim 1 wherein the disinfecting alcohol is a $C_{1-6}$ alcohol or mixtures thereof.

12. The composition of claim 1 wherein the disinfecting alcohol is selected from the group consisting of methanol, ethanol, isopropyl alcohol, n-butanol, n-propyl alcohol, and mixtures thereof.

13. The composition of claim 1 wherein the gelling-agent is present in an amount of about 0.1% to about 3%, by weight.

14. The composition of claim 1 wherein the gelling agent is present in an amount of about 0.25% to about 2.5%, by weight.

15. The composition of claim 1 wherein the gelling agent comprises a natural gum, a synthetic polymer, a clay, an oil, a wax, and mixtures thereof.

16. The composition of claim 1 wherein the gelling agent is selected from the group consisting of an acrylate homopolymer, an acrylate copolymer, a carbomer, a polyacrylic acid, cellulose, a cellulose derivative, guar, a guar derivative, algin, an algin derivative, a water-insoluble $C_8$–$C_{20}$ alcohol, carrageenan, and mixtures thereof.

17. The composition of claim 1 wherein the geling agent comprises a polyacrylic acid, a polyacrylate, a smectite clay, or a polyquaternium compound.

18. The composition of claim 1 having a pH of about 5 to about 8.

19. The composition of claim 1 having a pH of about 6 to about 8.

20. An antimicrobial composition comprising:
(a) about 0.05% to about 5%, by weight, of a phenolic antibacterial agent;
(b) about 1% to about 40%, by weight, of a disinfecting alcohol;
(c) about 0.1% to about 5%, by weight, of a gelling agent; and
(d) water,
wherein the composition is free of a surfactant,
and wherein the composition has a log reduction against Gram positive bacteria of at least 2 after 30 seconds of contact, as measured against S. aureus, or has a log reduction against Gram negative bacteria of at least 2.5 after 30 seconds of contact, as measured against E. coli.

21. An antibacterial composition comprising:
(a) about 0.05% to about 5%, by weight, of a phenolic antimicrobial agent;
(b) about 1% to about 40%, by weight, of a disinfecting alcohol;
(c) about 0.1% to about 5%, by weight, of a gelling agent;
(d) 0.1% to about 30%, by weight, of a hydrotrope selected from the group consisting of sodium cumene sulfonate, ammonium cumene sulfonate, ammonium xylene sulfonate, potassium toluene sulfonate, sodium toluene sulfonate, sodium xylene sulfonate, toluene sulfonic acid, xylene sulfonic acid, sodium polynaphthalene sulfonate, sodium polystyrene sulfonate, sodium methyl naphthalene sulfonate, disodium succinate, and mixtures thereof; and
(e) water,
wherein the composition is free of a surfactant,
and wherein the antimicrobial agent is present in an amount of at least 25% of saturation concentration, when measured at room temperature.

22. The composition of claim 21 having a log reduction against Gram positive bacteria of at least 2 after 30 seconds of contact, as measured against S. aureus, and a log reduction against Gram negative bacteria of at least 2.5 after 30 seconds of contact, as measured against E. coli.

23. The composition of claim 21 wherein the antibacterial agent is present in an amount of at least 50% of saturation concentration.

24. The composition of claim 21 wherein the antibacterial agent is present in an amount of at least 75% of saturation concentration.

25. The composition of claim 21 wherein the antibacterial agent is present in an amount of at least 95% of saturation concentration.

26. The composition of claim 21 wherein the hydrotrope is present in an amount of about 0.5% to about 25% by weight.

27. The composition of claim 21 wherein the gelling agent comprises a natural gum, a synthetic polymer, a clay, an oil, a wax, and mixtures thereof.

28. The composition of claim 21 further comprising about 0.1% to about 50%, by weight, of a polyhydric solvent selected from thee group consisting off a diol, a triol, and mixtures thereof.

29. The composition of claim 28 wherein the polyhydric solvent comprises ethylene glycol, propylene glycol, glycerol, diethylene glycol, dipropylene glycol, tripropylene glycol, hexylene glycol, butylene glycol, 1,2,6-hexanetriol, sorbitol, PEG-4, or mixtures thereof.

30. The composition of claim 21 having a pH of about 5 to about 8.

31. The composition of claim 21 comprising:
(a) about 0.25% to about 2%, by weight, of the antimicrobial agent;
(b) about 5% to about 30%, by weight, of a disinfecting alcohol;
(c) about 0.25% to about 2.5%, by weight, of the gelling agent; and
(d) about 1% to about 20%, by weight, of the hydrotrope.

32. The composition of claim 31 having a pH of about 6 to about 8.

33. An antibacterial composition comprising:
(a) about 0.05% to about 5%, by weight, of a phenolic antimicrobial agent;
(b) about 1% to about 40%, by weight, of a disinfecting alcohol;
(c) about 0.1% to about 5%, by weight, of a gelling agent;
(d) 0.1% to about 30%, by weight, of a hydrotrope selected from the group consisting of sodium cumene sulfonate, ammonium cumene sulfonate, ammonium xylene sulfonate, potassium toluene sulfonate. sodium toluene sulfonate, sodium xylene sulfonate, toluene sulfonic acid, xylene sulfonic acid, sodium polynaphthalene sulfonate, sodium polystyrene sulfonate, sodium methyl naphthalene sulfonate, disodium succinate, and mixtures thereof; and
(e) water,
wherein the composition is free of a surfactant,
and wherein the composition has a log reduction against Gram positive bacteria of at least 2 after 30 seconds of contact, as measured against S. aureus, or has a log reduction against Gram negative bacteria of at least 2.5 after 30 seconds of contact, as measured against E. coli.

34. An antibacterial composition comprising:
(a) about 0.05% to about 5%, by weight, of a phenolic antimicrobial agent;
(b) about 1k to about 40%, by weight, of a disinfecting alcohol;
(c) about 0.1% to about 30%, by weight, of a hydrotrope selected from the group consisting of sodium cumene sulfonate, ammonium cumene sulfonate, ammonium xylene sulfonate, potassium toluene sulfonate, sodium toluene sulfonate, sodium xylene sulfonate, toluene sulfonic acid, xylene sulfonic acid, sodium polynaphthalene sulfonate, sodium polystyrene sulfonate, sodium methyl naphthalene sulfonate, disodium succinate, and mixtures thereof; and
(d) water,
wherein the composition is free of a surfactant,
and wherein the antimicrobial agent is present in an amount of at least 25% of saturation concentration, when measured at room temperature.

35. The composition of claim 34 having a log reduction against Gram positive bacteria of at least 2 after 30 seconds of contact, as measured against S. aureus, and a log reduction against Gram negative bacteria of at least 2.5 after 30 seconds of contact, as measured against E. coli.

36. The composition of claim 34 wherein the antibacterial agent is present in an amount of at least 75% of saturation concentration.

37. The composition of claim 34 wherein the antibacterial agent is present in an amount of at least 95% of saturation concentration.

38. An antibacterial composition comprising:
(a) about 0.05% to about 5%, by weight, of a phenolic antimicrobial agent;
(b) about 1% to about 40%, by weight, of a disinfecting alcohol;
(c) about 0.1% to about 30%, by weight, of a hydrotrope selected from the group consisting of sodium cumene sulfonate, ammonium cumene sulfonate, ammonium xylene sulfonate, potassium toluene sulfonate, sodium toluene sulfonate, sodium xylene sulfonate, toluene sulfonic acid, xylene sulfonic acid, sodium polynaphthalene sulfonate, sodium polystyrene sulfonate, sodium methyl naphthalene sulfonate, disodium succinate, and mixtures thereof; and
(d) water,
wherein the composition is free of a surfactant,
and wherein the composition has a log reduction against Gram positive bacteria of at least 2 after 30 seconds of contact, as measured against S. aureus, or has a log reduction against Gram negative bacteria of at least 2.5 after 30 seconds of contact, as measured against E. coli.

39. A method of reducing a bacteria population on a surface comprising contacting the surface with a composition of claim 1 for a sufficient time to provide a log reduction of bacteria of at least 2 against S. aureus and at least 2.5 against E. coli, then rinsing the composition from the surface.

40. The method of claim 39 wherein the surface is a skin of a mammal.

41. The method of claim 39 wherein the surface is a hard, inanimate surface.

42. The method of claim 39 wherein the composition contacts the surface for 30 seconds to achieve a log reduction of at least 2-against S. aureus.

43. The method of claim 39 wherein the composition contacts the surface for 60 seconds to achieve a log reduction of at least 3 against S. aureus.

44. The method of claim 39 wherein the composition contacts the surface for 30 seconds to achieve a log reduction of at least 2.5 against E. coli.

45. The method of claim 39 wherein the composition contacts the surface for 60 seconds to achieve a log reduction of at least 3.75 against E. coli.

46. A method of reducing a bacteria population on a surface comprising contacting the surface with a composition of claim 21 for a sufficient time to provide a log reduction of bacteria of at least 2 against *S. aureus* and at least 2.5 against *E. coli,* then rinsing the composition from the surface.

47. The method of claim 46 wherein the composition contacts the surface for 30 seconds to achieve a log reduction of at least 2 against *S. aureus.*

48. The method of claim 46 wherein the composition contacts the surface for 60 seconds to achieve a log reduction of at least 3 against *S. aureus.*

49. The method of claim 46 wherein the composition contacts the surface for 30 seconds to achieve a log reduction of at least 2.5 against *E. coll.*

50. The method of claim 46 wherein the composition contacts the surface for 60 seconds to achieve a log reduction of at least 3.75 against *E. coil.*

51. The method of claim 46 wherein the composition contacts the surface for 30 seconds to achieve a log reduction of at least 2 against *K. pneum.*

52. A method of reducing a bacteria population on a surface comprising contacting the surface with a composition of claim 31 for a sufficient time to provide a log reduction of bacteria of at least 2 against *S. aureus* and at least 2.5 against *E. coli,* then rinsing the composition from the surface.

53. The method of claim 52 wherein the composition contacts the surface for 30 seconds to achieve a log reduction of at least 2 against *S. aureus.*

54. The method of claim 52 wherein the composition contacts the surface for 60 seconds to achieve a log reduction of at least 3 against *S. aureus.*

55. The method of claim 52 wherein the composition contacts the surface for 30 seconds to achieve a log reduction of at least 2.5 against *E. coli.*

56. The method of claim 52 wherein the composition contacts the surface for 60 seconds to achieve a log reduction of at least 3.75 against *E. coli.*

57. The method of claim 52 wherein the composition contacts the surface for 30 seconds to achieve a log reduction of at least 2 against *K. pneum.*

* * * * *

UNITED STATES PATENT AND TRADEMARK OFFICE
CERTIFICATE OF CORRECTION

PATENT NO. : 6,136,771
DATED : October 24, 2000
INVENTOR(S) : Taylor et al.

It is certified that error appears in the above-identified patent and that said Letters Patent is hereby corrected as shown below:

Column 22, line 61, replace "saturationconcentration" with "saturation concentration".

Column 23, line 51, replace "R'1" with "R'$_1$".

Column 25, line 15, replace "thee" with "the".

Column 25, line 44, replace "." with ",".

Column 25, line 61, replace "1k" with "1%".

Column 26, line 55, replace "2-against" with "2 against".

Signed and Sealed this

Twenty-second Day of May, 2001

NICHOLAS P. GODICI

*Attest:*

*Attesting Officer*  *Acting Director of the United States Patent and Trademark Office*